United States Patent [19]

Ferrante et al.

[11] 4,255,256

[45] Mar. 10, 1981

[54] MEDIUM FOR THE SEPARATION OF HUMAN BLOOD LEUCOCYTES

[76] Inventors: Antonio Ferrante, 59 Gleneagles Rd., Mount Osmond, South Australia; Yee H. Thong, 27 Ward St., North Adelaide, South Australia, both of Australia

[21] Appl. No.: 96,661

[22] Filed: Nov. 23, 1979

[30] Foreign Application Priority Data

Dec. 13, 1978 [AU] Australia .................... PD7101

[51] Int. Cl.$^3$ .................... B01D 21/01; B01D 21/26
[52] U.S. Cl. .................... 210/730; 210/927; 210/789; 210/731
[58] Field of Search ............ 23/230 B; 128/2 F, 2 G, 128/DIG. 5; 210/49, 52, 54, 78, 83, 84, DIG. 23, DIG. 24; 233/1 R, 1 A, 26

[56] References Cited

U.S. PATENT DOCUMENTS

| | | | |
|---|---|---|---|
| 3,291,693 | 12/1966 | Brown | 210/DIG. 23 |
| 3,513,976 | 5/1970 | James | 210/DIG. 24 |
| 3,519,400 | 7/1970 | Anderson | 210/DIG. 24 |
| 3,814,687 | 6/1974 | Ellis et al. | 210/52 X |
| 4,027,660 | 6/1977 | Wardlaw et al. | 210/83 X |
| 4,083,784 | 4/1978 | Zine, Jr. | 210/DIG. 23 |
| 4,190,535 | 2/1980 | Luderer et al. | 210/83 |

*Primary Examiner*—Robert H. Spitzer
*Attorney, Agent, or Firm*—Brown & Martin

[57] ABSTRACT

A rapid one-step density separation method for separating and purifying whole blood into mononuclear and polymorphonuclear leucocyte and erythrocyte fractions wherein use is made of a separating medium consisting of a single aqueous solution of a high molecular weight sucrose or glucose polymer, and a water soluble metrizoate or diatrizoate compound, the density of the solution being greater than 1.095 gm/ml at room temperature and the concentration of the sucrose or glucose polymer lying in the range of 5 to 10% (based on weight/total volume of solution).

8 Claims, No Drawings

MEDIUM FOR THE SEPARATION OF HUMAN BLOOD LEUCOCYTES

This invention relates to a method of separation of the leucocyte populations of human blood, and more particularly to a rapid one-step density separation method of mononuclear leucocytes, polymorphonuclear leucocytes and erythrocytes (red blood cells) using a separating medium consisting of a single aqueous solution of (i) an erythrocyte aggregating or clumping agent and (ii) a compound which is highly soluble in water and gives a solution of relatively high density and relatively low viscosity and osmolarity.

BACKGROUND OF THE INVENTION

The Applicants are aware of a number of different techniques and methods used in the separation and purification of blood cell populations (and sub-populations). One of the most commonly used techniques for separating the white blood cells (leucocytes) from the red blood cells (the erythrocytes) is to simply mix a sample of blood with a solution which aggregates the red blood cells to thereby increase their rate of sedimentation. The density of the separating fluid is such that the sedimentation of the white blood cells is only partially affected and can be collected from the upper part of the separation fluid when the red blood cells have sedimented.

A more recently developed technique makes use of a system where the red blood cell aggregating agent is not actually mixed with the blood but rather the blood sample is carefully layered onto the top of the separating fluid medium whereupon the red blood cells are caused to agglutinate or aggregate at the interface and sediment to the bottom of the tube in which the medium is placed. There are several well known high polymer compounds which agglutinate the red blood cells, for example FICOLL 400 (registered Trade Mark of Pharmacia Fine Chemicals, Sweden) which is a neutral highly branched, high molecular weight polymer of sucrose, and these are generally mixed with a compound, in solution, of relatively high density and relatively low viscosity, for example sodium metrizoate or sodium diatrizoate. The separation can be carried out at unit gravity or by centrifugation. The majority of the white blood cells remain at the interface but such previous systems have not been effective in fractionating the white blood cell subpopulations, namely the mononuclear and the polymophonuclear cells—at least not in a one-step process using a separating medium of single density. In order to achieve such separation, one known method involves the isolation of the mononuclear white blood cells by centrifugation as a first step using a Isopaque-Ficoll (registered Trade Mark) mixture (Isopaque solution being obtained from Nyegaard & Co. of Norway and having as its main component sodium metrizoate) followed by separation of the polymorphonuclear white blood cells by using dextran or gelatin in order to sediment the red blood cells. Other known methods have used dextran sedimentation as a first step to obtain mixed white blood cells (leucocytes), followed by a second step of centrifugation using a Isopaque-Ficoll density gradient medium in order to separate the white blood cell sub-populations. A further step is required to lyse contaminating red blood cells with ammonium chloride in order to obtain relatively pure polymorphonuclear cells. It is also known to make use of a discontinuous density gradient where 2 or more separating solutions of different densities are layered on top of one another. The densities are selected so as to provide a (discontinuous) gradient over the desired range.

In another reported development, a one-step process was used but was only effective in separating the mononuclear leucocytes from the whole blood sample. For example, it was known to use a separation medium consisting of a mixture of Hypaque-Ficoll having a density of 1.077 g/ml onto which the blood sample was layered. Following centrifugation of the blood, the red blood cells and the polymorphonuclear leucocytes sedimented to the bottom while the mononuclear leucocytes formed a band at the interface. The separated fraction of mononuclear white blood cells was separately recovered by pipetting off the interface layer. The principles of density separation of the blood cell populations by the centrifugation method is well known to those skilled in the art and hence need not be discussed in any detail.

BRIEF SUMMARY OF THE APPLICANT'S INVENTION

The Applicants have discovered that by carefully controlling both the specific gravity of the separating fluid medium, and the concentration of the erythrocyte aggregating agent (based on weight/total volume) one is able in a single step to isolate the M.N (mononuclear) and P.M.N. (polymorphonuclear) white blood cell fractions and also the fraction of red blood cells.

It is the main object of this invention therefore to provide a rapid one-step process for the simultaneous isolation of the mononuclear leucocytes, the polymorphonuclear leucocytes and erythrocytes from whole blood using a single separating aqueous solution without a discontinuous density gradient.

According to this invention therefore, there is provided a one-step method of density separation of whole blood into (i) mononuclear leucocyte (ii) polymorphonuclear leucocyte and (iii) erythrocyte fractions wherein a whole blood sample is layered onto an aqueous separating medium in a centrifuge tube and the blood sample and separating medium centrifuged so that the whole blood sample is fractionalised into the fractions hereinabove, wherein the separating medium consists of a mixture of (a) an aqueous solution of an erythrocyte aggregating or clumping agent being a high molecular weight sucrose or glucose polymer and (b) a solution of a water soluble metrizoate-or diatrizoate-compound of relatively high density and relatively low viscosity and osmolarity, wherein (i) the density of the solution mixture (a) and (b) is greater than 1.095 gm/ml at room temperature, and (ii) the concentration of (a) lies in the range 5 to 11% (based on the weight per total volume of solution mixture).

The one-step procedure according to this invention has significant advantages over prior art methods. Firstly, it is very simple and rapid requiring only some thirty minutes for completion and may be performed by an inexperienced person. Secondly, relatively pure populations of both MN and PMN leucocytes are obtained. Thirdly, very high yields of both white cell types are obtained and it has been shown that no red blood cell contamination of the PMN fraction occurs so that ammonium chloride lysis and its possible adverse effects on neutrophils is not required. Finally, the immunological integrity of the cells is preserved and hence one is able to obtain a much healthier cell (sub) population as a result of less handling and more rapid separation.

With this invention, a very unexpected result is achieved—the blood cells are separated—by a one-step process—into three distinct fractions, there being one band at the blood sample—separating medium interface, a further band just below the top band with the more dense red blood cells forming the sediment. The top band contains the mononuclear leucocytes whilst the band therebelow contains the heavier PMN leucocytes cells.

In order to further describe and illustrate the present invention, we set out hereunder several examples which describe the method by which the invention can be carried out.

In this example, a separating fluid medium is prepared from a solution of Hypaque 85% (a sterile aqueous solution of 28.33% sodium 3,5-diacetamido-2,4,6-triiodoben-zoate, and 56,67% n-methylglucamine 3,5-diacetamido 2,4,6 triiodoben-zoate, purchased from Winthrop Laboratories, New South Wales, Australia) and Ficoll 400 (Pharmacia, Sweden) dissolved in distilled water at a concentration of 10% weight per volume. The separating medium consisted of 20 mls of Hypaque 85% and 90 mls of 10% aqueous Ficoll, the density of the mixture being 1.114 g/ml at room temperature.

For the centrifugation process, sterile, disposable 15×105 mm (diameter:length) plastic tubes were used. To each test tube was added 3 mls of the separating liquid medium. Using a pipette, 5 to 6 mls of heparinised whole human blood, obtained by vene-puncture, was then carefully layered onto the top of the separating medium to give a blood column height of 3.5 mm. The test tubes were then spun in a conventional centrifuge with swing-out buckets (in which the tubes are supported) at 200 g for twenty to thirty minutes at room temperature. Both the spinning time and speed can of course be varied as is well known to one skilled in the art. After centrifugation, 3 distinct blood cell layers or bands were observed. The layer at the interface was shown to consist of mononuclear leucocyte cells, the middle layer of polymorphonuclear leucocyte cells, and the bottom layer of erythrocytes which had sedimented to the bottom of the tube. The two leucocyte bands were then removed separately with different pipettes and washed thrice and resuspended in a known medium. Table 1 shows the relative number of leucocyte types in the upper two layers, the results being expressed as the mean ± standard deviation of 5 experiments using whole (peripheral) blood obtained from 5 different normal individuals.

TABLE 1

CELL TYPES IN THE MONONUCLEAR AND POLYMORPHONUCLEAR CELL FRACTIONS.

| Cell Fractions | Differential count (%) | | | | |
|---|---|---|---|---|---|
| | Lymphocytes | Monocytes | Basophils | Neutrophils | Eosinophils |
| Fr 1 (interface) | 83.9±1.6 | 13.8±2.3 | 0.5±0.5 | 1.8±0.8 | — |
| Fr 2 | 1.2±0.4 | — | — | 96.4±1.0 | 2.4±1.0 |

Total leucocyte recovery was greater than 80% in all experiments and cell viability exceeded 98%. The immunological function of the lymphocytes and neutrophils purified by this procedure was shown to have remained intact.

Further experiments carried out by the applicants have shown that in order to get satisfactory separation of the MN and PMN blood cells, the density of the separating solution must be greater than 1.095 gms per ml. Tests carried out for separating solutions with densities ranging from 1.080 to 1.20 gm/ml at a given concentration of Ficoll 400 clearly established that satisfactory separation of the cell fractions occurred only in those instances where the density of the separating solution exceeds 1.095 gms per ml.

The distance between the bands of MN and PMN fractions was shown to be approximately proportional to the height of the blood sample (above the separation mixture) in the tube; that is, the greater the height of the whole blood column, the further apart will be the bands. Tests also showed that, for a given height of blood sample in a tube, the distance between the bands of MN and PMN leucocytes remained approximately constant for any tube diameter.

It was also shown that the concentration of the aqueous Ficoll should be 7% or more (based on weight per total volume of separating solution used)—preferably 9% but not more than 11%. It will of course be appreciated by those skilled in the art that the concentration of Ficoll cannot be too high as highly viscous solutions effect the blood cell functions and also cause clumping of the blood cells which has a deleterious effect on the fractionalisation process.

Best results have been obtained with a Ficoll-Hypaque separating solution which has a density of 1.114 grams per ml (at room temperature) and 9% (w/v) Ficoll.

Further experiments conducted by the Applicants established that the Hypaque 85% solution used to suitably adjust the density of the Ficoll solution, can be replaced by other supporting medium aqueous solutions such as sodium metrizoate sodium diatrizoate, meglumine (N-methylglucamine) metrizoate or meglumine diatrizoate, and mixtures thereof. Solution mixtures of meglumine diatrizoate or meglumine metrizoate with sodium metrizoate or diatrizoate (and the Ficoll solution) were shown to give more clearly defined bands of leucocyte fractions in comparison with a separating medium consisting of aqueous Ficoll and an unmixed sodium metrizoate or sodium diatrizoate solution. All of these supporting mediums are highly soluble in water and give solutions of relatively high density and relatively low viscosity and osmolarity and hence are suitable for admixture with Ficoll so as to produce high density solutions without unduly affecting (i.e. increasing) the final viscosity of the separating aqueous mixture.

Similar experiments carried out by the Applicants have shown that the erythrocyte aggregating agent can also be aqueous Dextran (Dextran being a glucose polymer of high molecular weight of up to about 370,000), in the separating fluid medium and still fractionalise (but less effectively) the blood cells into the MN and PMN leucocytes and erythrocyte fractions. However, the concentration range of the Dextran (m.w. 264,000—Sigma Chemical Co., U.S.A.), (based on weight/total volume of separating solution), within which satisfactory results were obtained, was found to differ slightly to that of Ficoll 400, and in fact was between 5 and 10% as compared with 7 and 11% for the Ficoll:Hypaque mixture. The density of the Dextran-containing separating solution, as with the Ficoll mixture, must also be above 1.095 gm/ml to produce the desired blood cell fractions.

A brief consideration of the above examples will indicate that the Applicants have been successful in providing a rapid one-step method using a single aqueous separating mixture having density and concentration values within certain prescribed limits. With this invention, one is able to very quickly and easily and effectively diagnose the sub-populations of the white blood cells for immunological purposes.

We claim:

1. A rapid one step method of density separation of whole blood into (i) mononuclear leucocyte (ii) polymorphonuclear leucocyte and (iii) erythrocyte fractions wherein a whole blood sample is layered onto an aqueous separating medium in a centrifuge tube and the blood sample and separating medium centrifuged so that the whole blood sample is fractionalised into the fractions hereinabove, wherein the separating medium consists of a mixture of (a) an aqueous solution of an erythrocyte aggregating or clumping agent being a high molecular weight sucrose or glucose polymer and (b) a solution of a water soluble metrizoate- or diatrizoate- compound of relatively high density and relatively low viscosity and osmolarity, wherein (i) the density of the solution mixture (a) and (b) is greater than 1.095 gm/ml at room temperature, and (ii) the concentration of (a) lies in the range of 5 to 11% (based on the weight per total volume of solution mixture).

2. A rapid one step method according to claim 1 wherein (a) is a sucrose polymer and the concentration of said sucrose polymer lies in the range of 7 to 11% (based on weight/total volume of solution).

3. A rapid one step method according to claim 2 wherein the sucrose polymer is Ficoll (Registered Trade Mark) having a molecular weight of approximate 400,000.

4. A method according to claim 1 wherein (a) is a glucose polymer, the concentration thereof being in the range of 5 to 9% (based on weight/total volume of solution).

5. A method according to claim 4 wherein said glucose polymer is Dextran (Registered Trade Mark) having a molecular weight of approximately 264,000.

6. A method according to claim 2 wherein (b) is a mixture of an aqueous solution of meglumine diatrizoate or meglumine metrizoate and an aqueous solution of sodium metrizoate or sodium diatrizoate.

7. A method according to claim 1 wherein the separating medium is an aqueous solution of Ficoll (Registered Trade Mark) having a concentration of between 7 and 11% (based on weight/total volume of solution), and Hypaque 85% (Registered Trade Mark), wherein the density of the solution is in the range of 1.095 to 1.20 gm/ml at room temperature.

8. A method according to claim 1 wherein the density of the solution is 1.114 gm/ml at room temperature.

* * * * *